(12) United States Patent
Leti et al.

(10) Patent No.: US 10,299,502 B2
(45) Date of Patent: May 28, 2019

(54) METHOD FOR PRODUCING AN EXTRACT OF A MATRIX OF VEGETABLE ORIGIN WITH A NON-IONIC AMPHIPHILIC COMPOUND AS EXTRACTION ADJUVANT IN AN AQUEOUS MEDIUM

(71) Applicant: PIERRE FABRE DERMO-COSMETIQUE, Boulogne-Billancourt (FR)

(72) Inventors: Mathieu Leti, Toulouse (FR); Anne Mandeau, Toulouse (FR)

(73) Assignee: PIERRE FABRE DERMO-COSMETIQUE, Boulogne Billancourt (FR)

( * ) Notice: Subject to any disclaimer, the term of this patent is extended or adjusted under 35 U.S.C. 154(b) by 0 days.

(21) Appl. No.: 15/553,048

(22) PCT Filed: Mar. 18, 2016

(86) PCT No.: PCT/EP2016/056037
§ 371 (c)(1),
(2) Date: Aug. 23, 2017

(87) PCT Pub. No.: WO2016/146837
PCT Pub. Date: Sep. 22, 2016

(65) Prior Publication Data
US 2017/0367393 A1    Dec. 28, 2017

(30) Foreign Application Priority Data
Mar. 18, 2015 (FR) ..................... 15 52248

(51) Int. Cl.
*A23L 33/105* (2016.01)
*C11B 1/10* (2006.01)
(Continued)

(52) U.S. Cl.
CPC .............. *A23L 33/105* (2016.08); *A61K 8/96* (2013.01); *A61K 8/97* (2013.01); *A61K 8/9789* (2017.08);
(Continued)

(58) Field of Classification Search
CPC .. C11B 1/02; C11B 1/10; C11B 13/00; A61K 2236/53; A61K 8/96; A23L 33/105
See application file for complete search history.

(56) References Cited

U.S. PATENT DOCUMENTS 6,365,601 B1    4/2002  Gaikar et al.
2012/0244585 A1*  9/2012  Kale .................. C11B 1/10
                                              435/134

FOREIGN PATENT DOCUMENTS

WO    WO 2009/077970 A1    6/2009
WO    WO 2013/184884 A1    12/2013

OTHER PUBLICATIONS

Huibers, P.D.T., et al., Prediction of Critical Micelle ConcentratinUsing a Quantitative Structure—Property Relationship Approach. 1. Nonionic Surfactants, 1996, Langmuir, vol. 12, No. 6, pp. 1462-1470 (Year: 1996).*

(Continued)

*Primary Examiner* — Yate' K Cutliff
(74) *Attorney, Agent, or Firm* — Birch, Stewart, Kolasch & Birch, LLP

(57) ABSTRACT

The invention relates to a method for producing an extract of a matrix of vegetable origin, particularly a plant, involving a solid-liquid extraction by means of an aqueous solution containing at least one, preferably agro-sourced, non-ionic amphiphilic compound, at a concentration at least equal to the minimum hydrotrope concentration thereof.

24 Claims, 3 Drawing Sheets

Solubilization curves of Sudan red

(51) Int. Cl.
  *A61K 8/97*   (2017.01)
  *A61K 36/00*  (2006.01)
  *A61K 8/96*   (2006.01)
  *A61Q 19/00*  (2006.01)
  *A61K 8/9789* (2017.01)
(52) U.S. Cl.
  CPC .............. *A61K 36/00* (2013.01); *A61Q 19/00* (2013.01); *C11B 1/10* (2013.01); *A23V 2002/00* (2013.01); *A23V 2300/14* (2013.01); *A61K 2236/00* (2013.01); *A61K 2236/53* (2013.01)

(56) References Cited

OTHER PUBLICATIONS

Kobayashi, T. et al., Synthesis of alkyl fucosides through beta-glucosidas-catalyzed condensatin of fucose and 1-alcohols, 1999, Biotechnology Letters, 21, pp. 105-109 (Year: 1999).*

Shinoyama, H, et al., Surface Active Properties of Heptyl beta-D-xyloside synthesized by Utilizing the transxylosyl activity of beta-xylosidase, 1991, The Chemical Society of Japan, Bull. Chem. Soc. Jpn., vol. 64, No. 1, pp. 291-291 (Year: 1991).*

International Search Report issued in International Application No. PCT/EP2016/056037 dated Jun. 1, 2016.

Product Data Sheet GLUCOPON 225 DK, XP055274089 (Aug. 31, 2013), URL:http://dewolfchem.com/wp-content/uploads/2013/08/Glucopon-225-DK-2.pdf.

Wu et al., "Supercritical Carbon Dioxide Extract Exhibits Enhanced Antioxidant and Anti-inflammatory Activities of Physalis Peruvians", Journal of Ethnopharmacology, vol. 108 (2006) pp. 407-413.

Chemat et al., "Green extraction of natural products (GENP2013)," Comptes Rendus Chimie, vol. 17, 2014 (available online Jan. 29, 2014), pp. 179-180, with English translation.

Coffman et al., "Self-Association of Nicotinamide in Aqueous Solution: Light-Scattering and Vapor Pressure Osmometry Studies," Journal of Pharmaceutical Sciences, vol. 85, No. 8, Aug. 1996 (abstract published in Advance ACS Abstracts, Jun. 15, 1996), pp. 848-853.

Sanghvi et al., "Stacking complexation by nicotinamide: A useful way of enhancing drug solubility," International Journal of Pharmaceutics, vol. 336, 2007 (available online Nov. 12, 2006), pp. 35-41.

Author Unknown, "Agrosolvants; Une opportunité de développement à saisir," Formule Verte, No. 8, Dec. 2011, pp. 28-32, with a summary in English.

* cited by examiner

METHOD FOR PRODUCING AN EXTRACT OF A MATRIX OF VEGETABLE ORIGIN WITH A NON-IONIC AMPHIPHILIC COMPOUND AS EXTRACTION ADJUVANT IN AN AQUEOUS MEDIUM

CROSS-REFERENCE TO RELATED APPLICATIONS

This application is a National Stage of PCT/EP2016/056037 filed on Mar. 18, 2016, which claims priority to Application No. 1552248 filed in France, on Mar. 18, 2015. The entire contents of all of the above applications are hereby incorporated by reference.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

The field of the present invention relates to a method for producing a vegetable matrix extract with a non-ionic amphiphilic compound as extraction aid in aqueous medium.

Solid-liquid extraction is the process consisting in extracting a substance present in a solid, in particular a plant, into a liquid solvent. Maceration, infusion and decoction are conventional solid-liquid extraction methods.

Solvents are liquids—at working temperature—having the property of dissolving, diluting or extracting other substances without chemically modifying said substances and without themselves being modified. They are used, in large amounts, for numerous other industrial applications (paints, detergents, coatings, phytosanitary products, etc.) and are conventionally of petrochemical origin.

However, dwindling oil reserves and stricter regulations on chemicals make it necessary to find more environmentally friendly alternatives.

Green extraction is based on the discovery and design of extraction processes that reduce energy consumption and allow the use of alternative solvents—agro-solvents—while guaranteeing safe, high-quality extracts useful as ingredients in the pharmaceuticals, cosmetics, agri-food, fine chemicals and biofuels industries (Green extraction of natural products (GENP2013), (2014), *Comptes Rendus Chimie*, 17, 179-180). In this context, the improvement of existing processes and the design of new processes are the subject of much work aimed at reducing the environmental impact of the extraction step, leading to the emergence and popularization of technologies such as extraction by ultrasound, microwaves, supercritical $CO_2$ and flash vacuum-expansion. In parallel, the search for alternative extraction solvents, of non-petrochemical origin, constitutes another path to improvement.

The market for agro-solvents derived from wood, field crops (starch- or sugar-producing) and oleaginous species is thus in full expansion, leading to terpene derivatives, alcohols (ethanol, butanol, 1,3-propanediol), furfural derivatives and methyl esters (*Formule Verte* No. 8, December 2011, pp. 28-32).

Water is a natural solvent considered to be renewable. However, its high polarity does not allow the extraction of certain lipophilic molecules of interest.

It is thus necessary to have new solvents for extracting compounds of different ranges of polarity (increasingly wide range of polarity, or optimization of extraction of lipophilic compounds).

Certain non-ionic amphiphilic compounds in aqueous solution allow, at sufficient concentration, solubilization of lipophilic compounds.

Nicotinamide, dimethyl isosorbide, alkyl polyglycosides and urea are examples of these non-ionic amphiphilic compounds. The potential of these compounds as solubilization aids for certain lipophilic molecules in aqueous medium has been explored (Sanghvi R., Evans D., Yalkowsky S. Stacking complexation by nicotinamide: a useful way of enhancing drug solubility.

(2007) 336: 35-41).

But the solubilization property is not sufficient to allow extraction of solutes from vegetable matrix. Indeed, in the field of plant extraction, the extraction solvent must penetrate the vegetable matrix, destroy the membranes and release the compounds into the impregnation solvent (phenomena of diffusion, desorption, dissolution, etc.), and allow diffusion of the matrix solute towards the liquid film surrounding the solid, and transfer towards the solvent (limiting step). Depending on the solvent used, the plant cell membranes are weakened to a greater or lesser extent, which may or may not allow the release of the compounds contained within said cells.

BRIEF SUMMARY OF THE INVENTION

The Applicant has shown that an aqueous solution of non-ionic amphiphilic compounds, used at sufficient concentration, makes it possible to extract solutes having different ranges of polarity, from vegetable matrix.

The present invention thus relates to a method for producing a vegetable matrix extract involving solid-liquid extraction with the aid of an aqueous solution containing at least one non-ionic amphiphilic compound, preferably agro-sourced, at a concentration at least equal to the minimum hydrotrope concentration thereof.

DETAILED DESCRIPTION OF THE INVENTION

Figure 1:
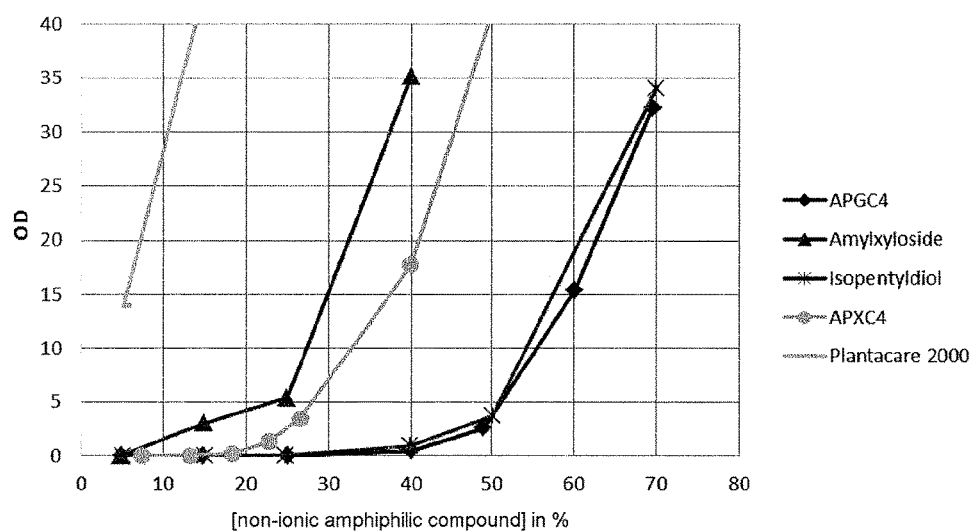
FIG. 1 shows the solubilization curves of Sudan red in aqueous solutions of non-ionic amphiphilic compounds at different concentrations.

The present invention relates to the production, with the aid of an aqueous solution of non-ionic amphiphilic compounds, of either a total extract containing polar, moderately polar and lipophilic compounds, or an extract enriched in lipophilic compounds of interest.

In the context of the present invention, the term "lipophilic compounds" refers to compounds having a positive octanol/water partition coefficient (also called log P or log $K_{ow}$).

According to the present invention, the term "non-ionic amphiphilic compound" refers to a compound that is water-soluble in any proportion and that does not have a surfactant property, to avoid the formation of micelles.

This extraction method is an alternative that makes it possible to replace polluting petrochemical organic solvents, such as ethyl acetate, hexane, acetone, etc., since the preferred non-ionic amphiphilic compounds can be agro-sourced, i.e., substantially derived from plant biomass.

The method according to the invention implements an extraction of vegetable matrix with the aid of an aqueous solution containing a non-ionic amphiphilic compound, preferably agro-sourced, at a minimum sufficient concentration, i.e., at a minimum hydrotrope concentration.

The term "minimum hydrotrope concentration" refers to the concentration above which these non-ionic amphiphilic compounds begin to form aggregates, i.e., new microenvironments with physical properties different from those observed when the compound is diluted, and different from micellar behavior. This minimum hydrotrope concentration is specific to each non-ionic amphiphilic compound and generally has the order of magnitude of the molarity. It can be determined by several physicochemical methods, such as by measuring surface tension, conductivity or dynamic and static light scattering (Self-association of nicotinamide in aqueous solution: Light-scattering and vapor pressure osmometry studies (1996) 85(8): 848-853), or quite simply by establishing a solubilization curve of a lipophilic compound (solubilized solute content as a function of concentration of non-ionic amphiphilic compound). Sudan red, a lipophilic dye easily measured by spectrophotometry, can be used as reference. The value of this concentration is dependent on the nature of the non-ionic amphiphilic compound and not of the solute. It corresponds to the minimal concentration above which the solubilization curve of the solute takes an exponential form.

According to another feature of the present invention, the aqueous solution containing said non-ionic amphiphilic compound, preferably agro-sourced, constitutes the only extraction solvent used.

According to an advantageous feature of the invention, solid-liquid extraction is performed by maceration of vegetable matrix in said aqueous solution containing at least one non-ionic amphiphilic compound at a minimum concentration at least equal to the minimum hydrotrope concentration, maintained under stirring.

According to the present invention, the expression "aqueous solution containing at least one non-ionic amphiphilic compound at a concentration at least equal to the minimum hydrotrope concentration" refers to an aqueous solution containing at least one non-ionic amphiphilic compound at a concentration greater than or equal to the above-mentioned minimum hydrotrope concentration (MHC). It is also necessary to take into account the water content possibly present in the vegetable matrix and, consequently, to adjust the concentration of the non-ionic amphiphilic compounds to enable their satisfactory use in the method according to the present invention.

According to another feature of the invention, the concentration of the non-ionic amphiphilic compound in said aqueous solution is between 1 and 10 times, preferably between 1 and 6 times, more preferably between 1 and 2 times, even more preferably between 1.4 and 1.8 times the minimum hydrotrope concentration. Advantageously, in practice the non-ionic amphiphilic compound can be used in an aqueous solution at a concentration equal to 1.5 mol/L.

According to another advantageous feature of the present invention, the non-ionic amphiphilic compound is present in the aqueous extraction solution at a concentration of less than 60% by weight relative to the weight of said solution, preferably less than 50% by weight relative to the weight of said solution, more preferably less than 40% by weight relative to the weight of said solution, even more preferably less than 30% by weight relative to the weight of said solution. It will be observed in particular that this concentration threshold implicitly precludes the use of ethanol as extraction solvent for lipophilic compounds, insofar as ethanol is generally used in much higher proportions, about 80%.

According to another feature of the invention, said aqueous solution is heated to a temperature ranging from 20° C. to reflux for a period of time varying from several minutes to several hours, depending on the extraction technique used.

According to another feature of the invention, the ratio between the vegetable matrix (expressed in kilograms) and said aqueous solution (expressed in liters) is between 1:5 and 1:50.

According to another feature of the invention, solid-liquid extraction is performed by any other extraction system well-known to a person skilled in the art, such as extraction by microwaves or ultrasound, or countercurrent extraction, etc.).

According to an advantageous feature of the invention, extraction is followed by solid-liquid separation by filtration or centrifugation.

According to an advantageous feature of the invention, said non-ionic amphiphilic compound, preferably agro-sourced, is an alkyl polyglycoside of general formula Alk-O-Zp, wherein:

Alk denotes a saturated or unsaturated, linear or branched hydrophobic aliphatic hydrocarbon fragment having 3 to 7 carbon atoms, and Z represents a hydrophilic glycoside group such as glucose, xylose, arabinose, and 1<p<5

According to a particular embodiment of the invention, Z represents a glucose group.

According to another particular embodiment of the invention, Z represents a xylose group.

According to yet another particular embodiment of the invention, Z represents an arabinose group.

According to a particular embodiment of the invention, Alk denotes a saturated or unsaturated, linear or branched hydrophobic aliphatic hydrocarbon fragment having 7 carbon atoms.

According to another particular embodiment of the invention, Alk denotes a saturated or unsaturated, linear or branched hydrophobic aliphatic hydrocarbon fragment having 6 carbon atoms.

According to yet another particular embodiment of the invention, Alk denotes a saturated or unsaturated, linear or branched hydrophobic aliphatic hydrocarbon fragment having 5 carbon atoms.

According to yet another particular embodiment of the invention, Alk denotes a saturated or unsaturated, linear or branched hydrophobic aliphatic hydrocarbon fragment having 4 carbon atoms.

According to another feature of the invention, the agro-sourced non-ionic amphiphilic compound is a combination of a C7 fatty alcohol derived from *Ricinus* and wheat glucose (non-GMO).

According to an advantageous feature of the invention, said compound is an amyl glycoside whose hydrophobic amyl fragment corresponds to a C5 alcohol obtained by fermentation of beet or of potato flour and whose glycoside fragment is derived from cereals.

According to an advantageous feature of the invention, said compound is a combination of a C4 fatty alcohol with a xyloside.

In the context of the present application, the abbreviation APG denotes an alkyl polyglucoside and the abbreviation APX denotes an alkyl polyxyloside, the two abbreviations optionally being followed by the notation Cx, x indicating the number of carbon atoms of the alkyl fragment.

In another particular embodiment of the invention, said non-ionic amphiphilic compound, preferably agro-sourced, is a diol selected from isopentyldiol (3-methyl-1,3-butanediol) and/or methylpropanediol, preferably isopentyldiol.

The non-ionic amphiphilic compound useful in the context of the present invention may advantageously be one of the commercial products Isopentyldiol (Kuraray) or Dub Diol (Stearinerie Dubois).

The present invention also relates to the use of an aqueous solution containing at least one non-ionic amphiphilic compound, preferably agro-sourced, at a concentration at least equal to a minimum hydrotrope concentration, as a solid-liquid extraction solvent of plants, fungi, lichens, algae, microalgae cultures or dedifferentiated plant cell cultures, preferably as the only extraction solvent. Said use relates to all the solvents and plant matrices mentioned in connection with the method of the invention.

According to the present invention, the term "vegetable matrix" refers to all or part of a plant, a fungus, a lichen, an alga, a microalgae culture or a dedifferentiated plant cell culture.

Said plant, fungus, lichen or algae is dried or fresh, frozen or thawed, and whole (neither crushed nor ground), crushed or ground. Said microalgae cultures or dedifferentiated plant cell cultures are whole, ground, preferably fresh but may be dried, filtered to recover the biomass, and optionally pretreated to release intracellular contents, for example by an ultrasonic method.

The term "plant part" notably refers to the aerial parts such as stems, branches, leaves, fruits, seeds and/or flowers; and/or the underground parts such as rhizomes, roots and/or bulbs.

The expression "lichen, fungus or alga part" refers to any organ of these organisms, such as thalli, fruiting bodies, macroscopic fruiting bodies, mycelia, and/or filaments.

In a particular embodiment of the invention, all or part of whole plants (neither crushed nor ground) will be used.

Among the plants useful in the context of the present invention, mention may be made of, inter alia: the fruits of *Physalis peruviana*, the fruits of *Embelia ribes*, the leaves of *Myrtus communis*, the underground parts and the leaves of *Piper* spp., the leaves of *Eucalyptus globulus*, the pericarps of *Garcinia mangostana*, the female inflorescences of *Humulus lupulus*, the bark of *Cinchona* sp., the aerial parts of *Urtica dioica*, the aerial parts of *Helichrysum* sp., the fruits of *Vanilla* sp., the rhizomes of *Curcuma* spp., the rhizomes of *Zingiber officinale*, the fruits and the leaves of *Olea europaea*.

The algae useful in the context of the present invention include in particular blue algae or cyanobacteria as well as eukaryotes including euglenophytes, cryptophytes, haptophytes, glaucophytes, red algae or Rhodophyta, stramenopiles notably including diatoms and brown algae or Phaeophyceae, and finally green algae which include, inter alia, Ulvophyceae.

Among the lichens useful in the context of the present invention, mention may be made of, inter alia: the thalli of *Cetraria islandica*, the thalli of *Usnea* spp., the thalli of *Cladonia* spp., and the thalli of *Lobaria* spp.

Among the fungi useful in the context of the present invention, mention may be made of, inter alia: *Coriolus versicolor*, *Cordyceps* spp.

Among the plant cell cultures useful in the present invention, mention may be made of, inter alia: *Mimosa pudica* cell cultures, *Tripterygium wilfordii* cell cultures.

At a certain concentration, the non-ionic amphiphilic compounds will, unexpectedly, make it possible to extract lipophilic compounds in water. This minimum hydrotrope concentration is specific to each non-ionic amphiphilic compound and may easily be determined by, for example, spectrophotometric assay of the solubilization of Sudan red. This minimum hydrotrope concentration is generally on the order of magnitude of the molarity.

Preferably, the non-ionic amphiphilic compounds are alkyl glycosides or alkyl polyglycosides.

The non-ionic amphiphilic compound useful in the context of the present invention may advantageously be one of the commercial raw materials SEPICLEAR G7® (SEPPIC) and APPYCLEAN® (WHEATOLEO). It may also be a xylose monomer fragment having an anomeric hydroxyl functional group substituted by a C4 alkoxy radical.

The extraction conditions (duration, concentration of the non-ionic amphiphilic compound, pH, temperature, etc.) may vary according to the plant/non-ionic amphiphilic compound pair so as to optimize extraction yield and/or selectivity. Such specific adaptations are the domain of persons skilled in the art using their general knowledge in the field of solid-liquid extraction.

Generally, the method consists in maceration under stirring, at temperatures ranging between 20° C. and reflux, of dry or fresh vegetable matrix ground in an aqueous solution containing a non-ionic amphiphilic compound at a concentration at least equal to the minimum hydrotrope concentration to allow extraction of lipophilic compounds.

According to a preferred embodiment, besides the aqueous solution of non-ionic amphiphilic compound, no other solvent is used in the extraction step itself. The aqueous solution of non-ionic amphiphilic compound, used at a specific concentration, is the only solvent used in the extraction method.

In a particular embodiment of the invention, the ratio of plant (kg) to solvent (L) is between 1:5 and 1:50. Of course, the marc can be re-extracted one or more times in order to exhaust the plant.

The extraction may be performed in a conventional reactor or assisted by any other extraction system well-known to persons skilled in the art (microwaves, ultrasound, countercurrent extraction, etc.).

The duration of extraction may vary from several minutes to several hours, depending on the extraction technique used.

The extraction may be applied to fresh vegetable matrix homogenized with the non-ionic amphiphilic compound while taking into account the moisture content of the vegetable matrix.

The extraction is followed by solid-liquid separation by centrifugation and/or filtration.

The term "centrifugation" refers to the action of separating the components of a mixture according to their difference in density by subjecting them to centrifugal force, by means of a decanter centrifuge or any type of centrifuge, in order to obtain a perfectly clear solution.

The term "filtration" refers frontal or tangential filtration, where the presence of a filtration aid (like pearlite or diatoms, etc.) may be envisaged. This filtration retains the last solid residues, the goal being to obtain a perfectly clear solution. It may be followed by membrane filtration with a cut-off defined according to the size of the molecules to be considered. It may also be replaced or followed by filtration on resin or silica, in order to enrich for the compound of interest, for example by using adsorption resins.

In a particular embodiment, the solution obtained after solid-liquid separation is preserved as such or is lyophilized, including the molecules of interest, as well as the non-ionic amphiphilic compound(s), said compound(s) allowing better solubilization of the extract in the final product.

Total extract containing compounds in a wide range of polarities (polar, moderately polar, non-polar) is thus obtained.

The extract thus obtained may also be diluted in a volume of water optionally supplemented with one or more adjuvants selected from salts, acids or bases, so as to be at a final concentration of non-ionic amphiphilic compound below the sufficient concentration defined above. Thus, it is possible to recover the lipophilic compounds by precipitation and solid-liquid separation such as filtration or centrifugation.

An extract enriched in lipophilic compounds is thus obtained. The lipophilic compounds of interest may be flavonoids, phenolic acids, terpene (mono-, di-, triterpenes) and steroid compounds, diarylheptanoid derivatives, lignans, coumarins, quinones, anthraquinones, xanthones, phloroglucinols, iridoids, sesquiterpene lactones, alkaloids, sucrose esters, polar lipids, etc.

They may be in particular kavalactones, myrtucommulones, embelin, quinine and derivatives thereof, vanillin and derivatives thereof, α-mangostin, xanthohumol, mono- and digalactosyldiacylglycerol, maslinic acid, ursolic acid, rosmarinic acid, carnosol, galangin, pinobanksin, cardamonin, curcuminoids, gingerol, shogaol.

The total extract or the extract enriched in lipophilic compounds may be diluted, concentrated, dried or preserved as such by adding a suitable, approved preservative to the desired final product (such as glycols, or sorbic acid, benzoic acid, citric acid and salts thereof, etc.) or alcohol (minimum 15°).

Vacuum drying, lyophilization or atomization technologies may be envisaged in order to produce dry extract. The extract obtained may be dried with or without substrate and/or solubilized in a liquid substrate.

The liquid, paste or dry extracts obtained as defined above can be used as such in cosmetic, pharmaceutical or food compositions intended for topical or oral administration.

The advantages are:
- if the filtrate is preserved as such or is lyophilized, production of total extract containing the molecules in a wide range of polarities, as well as the non-ionic amphiphilic compounds, allowing better solubilization of the extract in the final product.
- if the lipophilic compounds are purified by precipitation, production of an extract enriched in lipophilic compounds obtained with the aid of aqueous extraction and of agro-sourced substances, alternative to toxic and petrochemical-based solvents such as hexane, ethyl acetate or acetone.

The following examples are provided for informational purposes and are not limiting.

EXAMPLES

Example 1: Enriched Extract of *Physalis peruviana*

100 g of dried and ground *Physalis* fruit is stirred for 2 h at 40° C. with 700 mL of 1.5 M aqueous heptylglucoside solution (SEPICLEAR G7®, SEPPIC). After filtration, the filtrate is acidified to pH 2 then diluted with 15 volumes of water. After centrifugation, the pellet is taken up and dried. The enriched extract is obtained with a yield of 2.1% by weight.

Example 2: Enriched Extract of *Physalis peruviana*

20 g of dried and ground *Physalis* fruit is stirred for 2 h at 40° C. with 140 mL of 0.75 M aqueous heptylglucoside solution. After filtration, the filtrate is diluted with 6.6 volumes of water. After centrifugation, the pellet is taken up and dried. The enriched extract is obtained with a yield of 0.64% by weight.

Example 3: Enriched Extract of *Physalis peruviana*

20 g of dried and ground *Physalis* fruit is stirred for 2 h at 40° C. with 140 mL of 3 M aqueous heptylglucoside solution. After filtration, the filtrate is diluted with 22 volumes of water. After centrifugation, the pellet is taken up and dried. The enriched extract is obtained with a yield of 0.98% by weight.

Results obtained for the various enriched extracts of *Physalis*:

| Extract | Yield | Sucrose ester content |
| --- | --- | --- |
| According to Example 1 | 2.11% | 19.5% |
| According to Example 2 | 0.64% | 16.4% |
| According to Example 3 | 0.98% | 16.2% |
| Ethyl acetate (1 h, reflux) | 2.04% | 12.9% |
| Heptane (1 h, reflux) | 1.04% | 3.0% |

In Examples 1 to 3, extraction of *Physalis* fruits with aqueous heptylglucoside solution followed by precipitation of the extract by dilution produces an extract enriched in sucrose esters. The sugars of the fruit are extracted but remain in solution during the dilution and do not precipitate. The quality of the extracts obtained is superior to the extracts obtained using solvents of petrochemical origin (ethyl acetate, heptane).

Example 4: Vanilla Extract 5 kg of dried and ground vanilla pods is extracted for 3 h at 50° C. with 50 L of 1.5 M aqueous heptylglucoside solution. After pressure filtration, the marc is rinsed with 25 L of the same solution. The filtrate is concentrated so as to obtain a vanilla extract in the form of a reddish-brown syrupy solution.

Results obtained for the vanilla extract:

| Extract | Yield | Vanillin and derivatives content |
|---|---|---|
| According to Example 4 | 800% | 0.3% |

This extract, on heptylglucoside substrate, contains a substantial proportion of vanillin and derivatives, while being pre-formulated so as to facilitate its introduction into the aqueous phase of a cosmetic, nutraceutical or medicinal formula.

Example 5: Enriched Extract of Mangosteen 100 kg of dried and ground pericarps of Garcinia mangostana is stirred for 2 hours at 40° C. with 1000 L of 1.5 M aqueous heptylglucoside solution. After filtration, the filtrate is acidified to pH=2 then diluted with 11 volumes of water acidified to pH=2. After centrifugation, the pellet is taken up and dried. The extract enriched in xanthones (21.3% expressed in α-mangostin) is obtained with a yield of 7.3% by weight. The extract obtained is tannin-free.

By comparison, ethanol reflux extraction of dried and ground pericarps of Garcinia mangostana with an identical plant mass/solvent volume ratio gives an extract with a lower xanthone content (19.5% expressed in α-mangostin) but a higher yield (27%). The extract obtained contains tannins.

By comparison, hexane reflux extraction of dried and ground pericarps of Garcinia mangostana with an identical plant mass/solvent volume ratio gives an extract with a higher xanthone content (89.1% expressed in α-mangostin) but a lower yield (1.2% by weight). The extract obtained is tannin-free.

Extraction with 1.5 M aqueous heptylglucoside solution thus allows selective extraction of xanthones in comparison with ethanol extraction. It also allows a higher extraction yield than with hexane extraction.

Example 6: Enriched Extract of Piper Methysticum 1 kg of dried and ground underground parts of Piper methysticum is extracted with 700 mL of 1.5 mol/L aqueous amyl xyloside solution (APXC5) for 1.5 hours under stirring at 40° C. After filtration, the filtrate is diluted with 4 volumes of water. After centrifugation, the pellet corresponding to the enriched extract of Kava is obtained with a yield of 6.2%. The extract contains 3.0% kavalactones.

By comparison, ethyl acetate reflux extraction of dried and ground underground parts of Piper methysticum with an identical plant mass/solvent volume ratio gives a yield of 8.2%. The extract contains 5.3% kavalactones.

By comparison, water reflux extraction of dried and ground underground parts of Piper methysticum with an identical plant mass/solvent volume ratio gives a yield of 23.1%. The extract contains 0.25% kavalactones.

The three extracts have a different kavalactone composition:

The extract obtained by extraction with the 1.5 mol/L aqueous amyl glycoside solution has a higher content of low-polarity kavalactones (yangonin, demethoxyyangonin, flavokavains A, B and C) than the ethyl acetate extract (44.8% compared with 35.3% of total kavalactones).

Conversely, the extract obtained by extraction with the 1.5 mol/L aqueous amyl glycoside solution has a lower content of the most polar kavalactones (methysticin, dihydromethysticin, kavain and marindinin) than the ethyl acetate extract (55.2% compared with 64.7% of total kavalactones).

The extract obtained by aqueous extraction contains 1.66% kavalactones and does not contain low-polarity kavalactones (yangonin, demethoxyyangonin, flavokavains A, B and C).

Extraction with 1.5 mol/L aqueous amyl glycoside solution thus allows selective extraction of the least polar kavalactones for a total yield comparable to ethyl acetate extraction.

| Example 7: Gelatin capsule | |
|---|---|
| Mangosteen extract according to Example 5 | 200 mg |
| Starch | 45 mg |
| Magnesium stearate | 2 mg |

| Example 8: Cream | |
|---|---|
| Vanilla extract according to Example 4 | 0.5-3% |
| Tribehenin PEG- 20 esters | 2-7% |
| Isodecyl neopentanoate | 2-9% |
| Glycerin | 0.5-10% |
| Glycol palmitate | 1-6% |
| Cetyl alcohol | 0.5-3% |
| Disodium EDTA | 0.05-0.25% |
| Preservatives | 0.5-3% |
| Fragrance | 0.2-0.5% |
| Xanthan gum | 0.1-0.4% |
| Water | qs |

Example 9: Exemplary Solubilization Curves

The solubilization curves of Sudan red in aqueous solutions of various non-ionic amphiphilic compounds at different concentrations were prepared. After saturation of the solutions with Sudan red and filtration, the Sudan red content solubilized in each solution is measured after dilution by UV spectrophotometry at 476 nm. The solubilization curves appear in the accompanying FIG. 1. The y axis represents OD values multiplied by dilution, these values being proportional to concentration (according to the Beer-Lambert law).

These curves make it possible to determine the minimum hydrotrope concentration of the non-ionic amphiphilic compounds according to the invention.

Plantacare (decyl glucoside) is unsuitable, having a clearly surfactant behavior (high solubilization at low concentration, the compound forming micelles). It would be impossible to recover the compounds of interest by dilution. Moreover, the foam formation provided by the surfactant considerably hinders filtration.

The shape of the curves obtained with α-mangostin according to a similar method (HPLC assay of solubilized α-mangostin) is comparable to those obtained with Sudan red, showing that this value depends on the amphiphilic compound and not on the solute.

Figure 2:
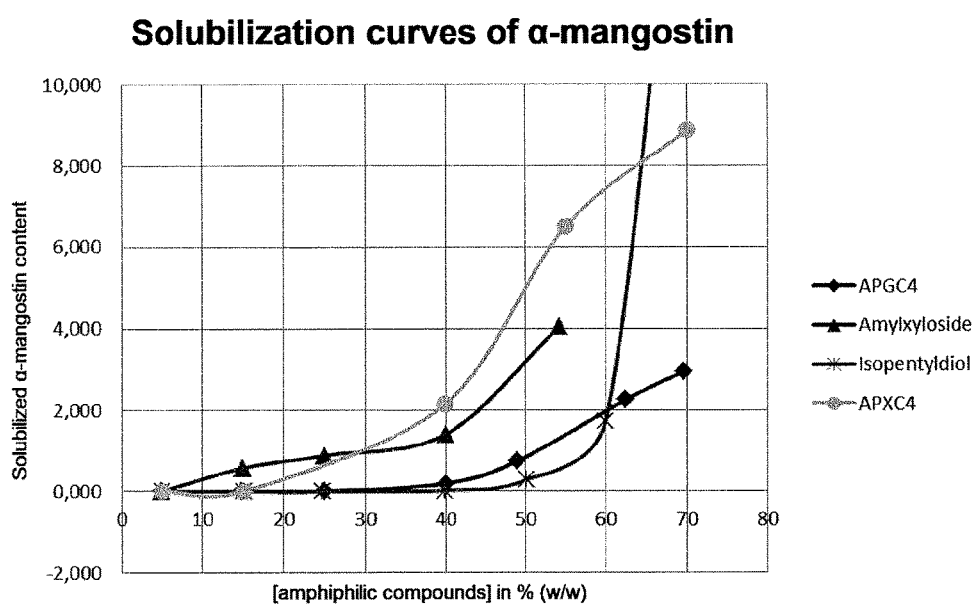
FIG. 2 shows the solubilization curves of α-mangostin in aqueous solutions of non-ionic amphiphilic compounds at different concentrations.

The solubilization curves of α-mangostin in aqueous solutions of non-ionic amphiphilic compounds at various concentrations appear in the accompanying FIG. 2.

It can thus be deduced from these curves that APXC4 has an MHC of 15-20%, and amyl xyloside of 5-10%.

The MHC of isopentyldiol is between 40 and 45%.

These values are necessary to implement the extraction method, such as for example the extraction of α-mangostin from mangosteen pericarps:

| Compound | Concentration | g of α-mangostin extracted % g of plant |
|---|---|---|
| APX C4 | 5% | 0.36 |
| APX C4 | 25% | 7.87 |
| Isopentyldiol | 59% | 6.59 |
| Amyl xyloside | 40% | 7.30 |
| AcOEt | 100% | 7.49 |

At 25% APXC4, the active substance content extracted from mangosteen pericarps is equivalent to that obtained by ethyl acetate reflux extraction, which is not the case at 5% (concentration below the MHC).

This active substance can then be recovered by dilution when the final concentration of amphiphilic compound is below the MHC, as can be seen in the following table:

| Compound | Extraction concentration | Concentration after dilution | % of α-mangostin recovered by precipitation/α-mangostin extracted |
|---|---|---|---|
| APX C4 | 25% | 9% | 86% |
| Isopentyldiol | 59% | 24% | 66% |
| Amyl xyloside | 40% | 15% | 12% |
|  |  | 7% | 100% |

By diluting the amyl xyloside solution to 15%, little α-mangostin precipitates, the concentration remaining above the MHC. At 7% amyl xyloside, 100% of the α-mangostin extracted precipitates.

Example 10

—Extraction of Fresh Olive Cake

Weigh 10 g of olive pulp ground after pressing to recover the oil (containing 76% water); add the equivalent of 12 g of APXC4 (dry matter) and water so as to be at a final APXC4 concentration of 50% (taking into account the water content of the plant). Heat for 3 h at 50° C. and filter to recover a clear, brown filtrate with a yield of 87.5%.

In parallel, lyophilize this same olive pulp (24.5% yield) and extract it with ethyl acetate for 1 h at reflux. After evaporation of the solvent, a cloudy, green oil is obtained with a yield of 23.4% dry matter and 5.7% fresh matter.

Evaluation of the extracts obtained by TLC under the following conditions:

Stationary phase: TLC plate coated with silica gel 60
Mobile phase: ethyl acetate/cyclohexane (1:1)
Developer: sulfuric vanillin+heating to 120° C.

Figure 3:
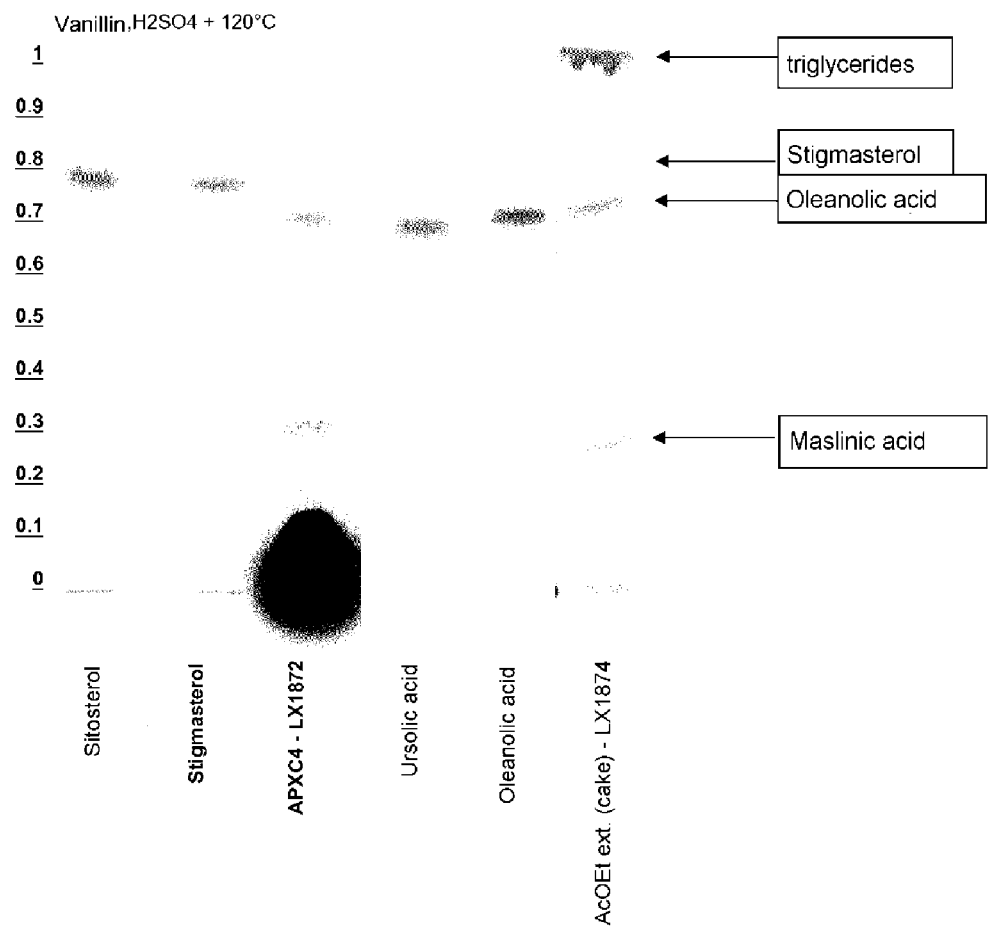
FIG. 3 shows the TLC profiles of different extractions of vanillin for triglycerides, stigmasterol, oleanolic acid and maslinic acid.

Comparison of the TLC profiles appearing in the accompanying FIG. 3 shows that the extract (LX 1872) with APXC4 contains triterpenes (oleanolic acid and maslinic acid), whereas the AcOEt extract (LX 1874) contains triglycerides in addition to triterpenes. The molecules of interest are thus present without having to dry the material and extract it with a toxic and volatile solvent. Moreover, neither chlorophyll nor neutral lipids are extracted.

The invention claimed is:

1. A method for producing a vegetable matrix extract, comprising:
   solid-liquid extraction of a vegetable matrix with an aqueous solution comprising at least one non-ionic amphiphilic compound,
   wherein said at least one non-ionic amphiphilic compound is an alkyl polyglycoside of general formula Alk-O-Zp, wherein:
   Alk represents a saturated or unsaturated, linear or branched hydrophobic aliphatic hydrocarbon fragment having 3 to 6 carbon atoms, and
   Z represents a hydrophilic glycoside group selected from the group consisting of glucose, xylose and arabinose, and
   $1<p<5$,
   wherein a concentration of the at least one non-ionic amphiphilic compound is greater than or equal to a minimum hydrotrope concentration of the at least one non-ionic amphiphilic compound, and
   wherein the at least one non-ionic amphiphilic compound does not form micelles.

2. The method as claimed in claim 1, wherein the aqueous solution constitutes the only extraction solvent used.

3. The method as claimed in claim 1, wherein the solid-liquid extraction is performed by maceration of the plant in said aqueous solution under stirring.

4. The method as claimed in claim 1, wherein the solid-liquid extraction is performed under microwaves, under ultrasound, or in a countercurrent process.

5. The method as claimed in claim 1, wherein the concentration of the at least one non-ionic amphiphilic compound in said aqueous solution is between 1 and 10 times the minimum hydrotrope concentration.

6. The method as claimed in claim 1, wherein the at least one non-ionic amphiphilic compound is in said aqueous solution at a concentration of less than 60% by weight relative to the weight of said aqueous solution.

7. The method as claimed in claim 1, wherein said aqueous solution is heated to a temperature ranging from 20° C. to reflux for a period of time varying from several minutes to several hours during the solid-liquid extraction.

8. The method as claimed in claim 1, wherein a ratio between the vegetable in kilograms and said aqueous solution in liters is between 1:5 and 1:50.

9. The method as claimed in claim 1, wherein the solid-liquid extraction is followed by solid-liquid separation by filtration or centrifugation.

10. The method as claimed in claim 1, wherein the at least one non-ionic amphiphilic compound is a combination of a $C_7$ fatty alcohol derived from *Ricinus* and wheat glucose (non-GMO).

11. The method as claimed in claim 1, wherein said at least one non-ionic amphiphilic compound is an amyl glycoside whose hydrophobic amyl fragment corresponds to a $C_5$ alcohol obtained by fermentation of beet or of potato flour and whose glycoside fragment is derived from cereals.

12. The method as claimed in claim 1, wherein the vegetable used is selected from the group consisting of fruits of *Physalis peruviana*, fruits of *Embelia ribes*, leaves of *Myrtus communis*, underground parts and leaves of *Piper* spp., leaves of *Eucalyptus globulus*, pericarps of *Garcinia mangostana*, female inflorescences of *Humulus lupulus*, bark of *Cinchona* sp., aerial parts of *Urtica dioica*, aerial parts of *Helichrysum* sp., fruits of *Vanilla* sp., rhizomes of *Curcuma* spp., rhizomes of *Zingiber officinale* and fruits and leaves of *Olea europaea*.

13. The method as claimed in claim 9, wherein a solution obtained after the solid-liquid separation is preserved, including molecules of interest, as well as the at least one non-ionic amphiphilic compound, said at least one non-ionic amphiphilic compound increase solubilization of the molecules of interest.

14. The method as claimed in claim 1, wherein in the extract obtained, lipophilic compounds are purified by precipitation.

15. The method as claimed in claim 1, wherein the vegetable matrix is a plant and the vegetable matrix extract is a plant extract.

16. The method as claimed in claim 1, wherein the at least one non-ionic amphiphilic compound is agro-sourced.

17. The method as claimed in claim 5, wherein the concentration of the at least one non-ionic amphiphilic compound in said aqueous solution is between 1 and 6 times the minimum hydrotrope concentration.

18. The method as claimed in claim 5, wherein the concentration of the at least one non-ionic amphiphilic compound in said aqueous solution is between 1 and 2 times the minimum hydrotrope concentration.

19. The method as claimed in claim 5, wherein the concentration of the at least one non-ionic amphiphilic compound in said aqueous solution is between 1.4 and 1.8 times the minimum hydrotrope concentration.

20. The method as claimed in claim 1, wherein the at least one non-ionic amphiphilic compound is present in said aqueous solution at a concentration of less than 50% by weight relative to the weight of said aqueous solution.

21. The method as claimed in claim 1, wherein the at least one non-ionic amphiphilic compound is present in said aqueous solution at a concentration of less than 40% by weight relative to the weight of said aqueous solution.

22. The method as claimed in claim 1, wherein the at least one non-ionic amphiphilic compound is present in said aqueous solution at a concentration of less than 30% by weight relative to the weight of said aqueous solution.

23. The method as claimed in claim 9, wherein a solution obtained after the solid-liquid separation is lyophilized, including molecules of interest, as well as the at least one non-ionic amphiphilic compound, said at least one non-ionic amphiphilic compound increase solubilization of the molecules of interest.

24. The method as claimed in claim 1, wherein molecules in the extract are precipitated by dilution of the at least one non-ionic amphiphilic compound in the aqueous solution after solid-liquid separation.

* * * * *